(12) United States Patent
Eek-Vancells

(10) Patent No.: US 7,005,529 B2
(45) Date of Patent: Feb. 28, 2006

(54) PROCESS FOR THE SEPARATION OF AN AQUEOUS MIXTURE OF TRIOXANE AND FORMALDEHYDE AND CORRESPONDING APPLICATIONS

(75) Inventor: Lluis Eek-Vancells, Barcelona (ES)

(73) Assignee: Patentes y Novedades, S.L., Barcelona (ES)

(*) Notice: Subject to any disclaimer, the term of this patent is extended or adjusted under 35 U.S.C. 154(b) by 110 days.

(21) Appl. No.: 10/468,084

(22) PCT Filed: Sep. 28, 2001

(86) PCT No.: PCT/ES01/00362

§ 371 (c)(1),
(2), (4) Date: Aug. 15, 2003

(87) PCT Pub. No.: WO02/066455

PCT Pub. Date: Aug. 29, 2002

(65) Prior Publication Data

US 2004/0242906 A1    Dec. 2, 2004

(30) Foreign Application Priority Data

Feb. 16, 2001   (ES) .............................. 200100353

(51) Int. Cl.
*C07D 309/00*    (2006.01)
(52) U.S. Cl. ..................... 549/568; 546/568
(58) Field of Classification Search ............. 546/568; 549/568

See application file for complete search history.

(56) References Cited

U.S. PATENT DOCUMENTS

| 3,281,336 A | | 10/1966 | Talbert |
| 3,494,106 A | * | 2/1970 | Herz et al. ................... 95/199 |
| 6,201,136 B1 | * | 3/2001 | Reichl et al. ................ 549/368 |
| 6,433,194 B1 | * | 8/2002 | Schweers et al. .......... 549/368 |

FOREIGN PATENT DOCUMENTS

EP    0680959    11/1995

* cited by examiner

*Primary Examiner*—Cecilia J. Tsang
*Assistant Examiner*—Raymond Covington
(74) *Attorney, Agent, or Firm*—Staas & Halsey LLP

(57) ABSTRACT

Process for the separation of an aqueous mixture of trioxane and formaldehyde and corresponding applications. The aqueous trioxane and formaldehyde mixture has first trioxane:formaldehyde ratio. The process includes the steps of reacting the aqueous mixture of trioxane and formaldehyde with urea, and separation an exiting vapor phase having a second trioxane:formaldehyde ratio that it higher than the first trioxane:formaldehyde ratio. An aqueous mixture of trioxane and formaldehyde coming from a reactor in which trioxane is being synthesized or from a distillation column in which a prior aqueous mixture of trioxane and formaldehyde can be separated from the excess formaldehyde. Raw material for the production of urea-formaldehyde glues or resins can be formed.

13 Claims, 1 Drawing Sheet

PROCESS FOR THE SEPARATION OF AN AQUEOUS MIXTURE OF TRIOXANE AND FORMALDEHYDE AND CORRESPONDING APPLICATIONS

BACKGROUND OF THE INVENTION

1. Field of the Invention

The invention relates to a process allowing mixtures of trioxane and formaldehyde in the presence of water, defining a first trioxane:formaldehyde ratio, to be separated.

2. Background Art

A number of steps is required for the preparation of trioxane, which explains the large number of patents published.

Generally speaking, trioxane is prepared starting out from formaldehyde by a trimerization reaction in the presence of an acid catalyst. In the reaction, together with the trioxane, there remains unreacted formaldehyde and water, which must be appropriately removed.

Trioxane is obtained, according to the conventional process, starting from aqueous solutions of formaldehyde the concentration of which can vary between 30 and 70%, when raising them to a boil in the presence of an acid catalyst, which causes a trimerization reaction of the formaldehyde according to the following equation:

3 $CH_2O \Longleftrightarrow (CH_2O)_3$

The extent of the reaction is highly dependent on the formaldehyde concentration in the solution and on the presence of trioxane therein. The greater the formaldehyde concentration and the smaller the trioxane content in the solution, the greater is the conversion.

The reaction takes place in a reactor and trioxane that is formed, in a relatively small amount due to the unfavorable balance, is vaporized together with the remaining components of the mixture and must be separated therefrom. The catalyst remains in the reactor, which receives, apart from the starting solution of formaldehyde, the residual currents of aqueous solutions of formaldehyde once this has been separated from the trioxane. This recirculating of residual currents of aqueous formaldehyde solutions lowers the yield of the reaction, because they dilute the formaldehyde solution contained in the reactor and they furthermore lower the conversion rate, since they are accompanied by a certain amount of trioxane that sets back the formation reaction thereof.

The vapors originated in the reactor pass to a distillation column at the head of which a mixture of trioxane, formaldehyde and water is obtained (that will hereinafter also be called an aqueous mixture of trioxane and formaldehyde, both if it is in the liquid phase and if it is in the vapor phase) in an approximate proportion of 30–40% trioxane, 17–30% formaldehyde and 40–50% water, which proportions depend on the conditions under which the reactor is operating. The excess formaldehyde in the form of an aqueous solution is extracted from the foot of the column and is recovered. The column distillate (i.e., the aqueous mixture of trioxane and formaldehyde) is extracted with a water-insoluble organic solvent, methylene chloride or benzene are examples of the most used, that dissolves the trioxane, whereby the formaldehyde is left in the remaining aqueous phase. The trioxane has to be recovered from these solutions in organic solvents by distillation and subsequent purification and the aqueous solution has to be treated to recover the formaldehyde.

Owing to the multiple possibilities available for carrying out the diverse steps a large number of patents have been published, each aimed at improving one or another aspect of the process. Thus, there are those that use strong inorganic acids, such as sulphuric acid or phosphoric acid, as catalyst of the trimerization reaction and those which use ion exchange resins in acid form, heteropolyacids, zeolites, montmorillonites and other solid catalysts that have silica as base, to mention only a few.

Whatever the catalyst used, the vapors that originate in the reactor are formed by a mixture of trioxane, formaldehyde and water mainly and small amounts of by-products such as methanol, formic acid, methyl formate, methylal, tetraoxane and dioxymethylene glycol dimethylether. The objective now is to separate the trioxane from the remaining products. In most patents this separation is achieved by means of a first step of fractional distillation that allows the vapors at the head of the column to be enriched in trioxane and a subsequent solvent extraction of the trioxane from said mixture. Other separation processes are based on the introduction of an inert gas into the mixture of vapors that facilitates the separation, azeotropic distillations with solvents or extractive distillations with water or glycols (U.S. Pat. No. 3,281,336) that retain the formaldehyde, or scrubbing of the gases at the exit from the reactor with heavy solvents that dissolve the trioxane (EP 0 680 959). There are further separation processes, such as distillation at two different pressures or simultaneous reaction-extraction or with gases in a supercritical state. This multiplicity of processes shows how hard it is to find an optimum process.

It should be pointed out that in all cases, with the exception of the extractive distillation with water or glycols, the trioxane is extracted from the mixture with water and formaldehyde, obtaining a trioxane solution in a solvent that must subsequently be removed in order to obtain pure trioxane. Only extractive distillation pursues the removal of the formaldehyde from the mixture and the release of the trioxane which separates out easily since it forms an azeotrope with the water that contains a high trioxane proportion. This is recovered by crystallization from said azeotropic mixture. It is a process which dispenses with the need for a solvent, whereby it eliminates the environmental problems that said solvents present. Nevertheless, it has an additional problem, which is that the aqueous formaldehyde solution obtained is highly dilute, whereby the formaldehyde has to be concentrated for later recovery thereof. If the process is carried out with a glycol or higher alcohol such as cyclohexanol, the formal obtained has to undergo a pyrolysis process to recover the formaldehyde. Both one case and the other require supplementary facilities and energy that complicate the process and make it more expensive.

SUMMARY OF THE INVENTION

It is an object of the present invention to overcome these drawbacks. This purpose is achieved by means of a process for the separation of an aqueous mixture of trioxane and formaldehyde, of the type first mentioned above and obtained preferably from the vapors produced in the trioxane formation reaction, including the step of reacting the aqueous mixture of trioxane and formaldehyde with urea and separating an exiting vapor phase and an exiting liquid phase, where the exiting vapor phase has a second trioxane:formaldehyde ratio that is higher than the first trioxane:formaldehyde ratio.

It has been observed that the vapors produced by a solution formed by trioxane, formaldehyde, urea and water contain more trioxane and less formaldehyde than the starting solution. In fact, practically all the formaldehyde can be retained with the urea and, on the other hand, the trioxane, together with water, passes to the vapor phase without appreciable amounts of formaldehyde, with the advantage of not having to use solvents or to add a formaldehyde separation and recovery step.

Thus, one way of separating the formaldehyde from the mixture of trioxane, formaldehyde, water and other compounds formed in the trioxane synthesis is by counterflow scrubbing of the vapors produced in the reactor with a concentrated solution of urea. The urea reacts with the formaldehyde to result in a urea-formaldehyde precondensate that later on, in another facility, will produce the glues or resins used in the fiber board, plywood or laminate industry.

The reaction between formaldehyde and the urea is favored in an alkaline medium, whereby it is advisable to add a certain amount of alkali together with the urea to the scrubbing solution, which in turn also helps to stabilize the resin solution obtained.

A further object of the present invention is the application of a process according to the invention for the separation of an aqueous mixture of trioxane and formaldehyde coming from a reactor in which trioxane is being synthesized, in particular when the trioxane is synthesized in the reactor starting from an aqueous solution of formaldehyde in the presence of an acid catalyst, and an aqueous mixture of trioxane and formaldehyde in vapor phase is formed.

It is also possible to apply a process according to the invention when the aqueous mixture of trioxane and formaldehyde comes from a distillation column in which a prior aqueous mixture of trioxane and formaldehyde is separated from the excess formaldehyde, in particular when a prior aqueous mixture of trioxane and formaldehyde coming from a reactor in which trioxane is being synthesized from an aqueous solution of formaldehyde is distilled in the distillation column.

Finally it is possible to use a process of the invention for obtaining raw material for the production of urea-formaldehyde glues or resins.

A further advantage is that a less impure trioxane is already obtained in this first step, because most of the impurities are retained in the urea solution, and where the low concentration of said impurities does not affect the quality of the resins that are subsequently obtained. The traces of trioxane that may remain have no influence either, since in the course of the manufacture of the resins, it converts to formaldehyde that reacts with the urea present.

BRIEF DESCRIPTION OF THE DRAWINGS

Further advantages and characteristics of the invention will be appreciated from the following examples and figures wherein, without any limitative character, some preferred embodiments of the invention are related. In the drawing.

DETAILED DESCRIPTION OF THE EMBODIMENTS

Figure 1:
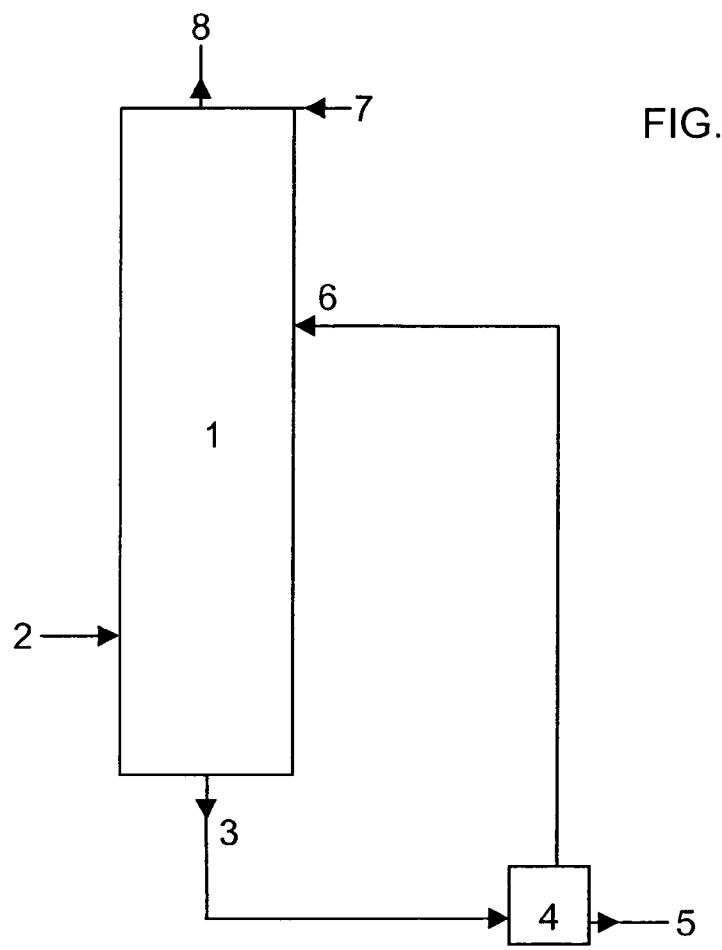
FIG. 1 is a schematic view of a scrubbing facility or column according to the invention.

One embodiment of the invention consists of reacting a concentrated formaldehyde solution in an acid medium in a reactor according to one or another of the existing processes and feeding the generated vapors to a scrubbing column. These vapors are supplied to a lower region of the column but at a certain height above the foot to obtain an appropriate exhaustion of trioxane. The purpose of the scrubbing column is to transfer mass and energy between the incoming vapor mixture (that is the aqueous mixture of trioxane and formaldehyde) and an aqueous solution of urea used as scrubbing liquid, at the same time as the formaldehyde and the urea react together chemically. To achieve this mass transfer the column is equipped with the appropriate devices normally used for such purpose, such as plates, or continuous fillers like those used in the conventional distillation columns. A concentrated urea solution and a dilute sodium hydroxide solution (or, optionally, any other strong base) are supplied to the head of the column in order to maintain a pH above 5, preferably between 7 and 9, in the solution that recirculates through the column. The formaldehyde and urea solution is collected at the foot of the column, mostly as a urea-formaldehyde precondensate. A part of said solution collected at the foot of the column, containing an amount of formaldehyde corresponding practically to the amount of formaldehyde that is supplied per unit of time into the column with the vapors produced in the reactor (i.e., with the aqueous trioxane and formaldehyde mixture), is removed from the system, and the rest of said solution collected at the foot of the column is recirculated to the upper region of the scrubbing column at a certain distance below the point where the fresh urea solution is supplied.

In this process there are four important parameters to keep in mind. These parameters are the amount of scrubbing liquid, the temperature of said liquid, the pH thereof and the urea concentration therein.

The amount of scrubbing liquid, as well as the concentration of urea, must be chosen so that the solution obtained at the foot of the scrubbing column maintains a formaldehyde to urea molar ratio of between 1:1 and 6:1, preferably between 4.5 and 5.5:1, so that the solution obtained at the foot is appropriate for the later synthesis of the desired glues or resins. Nevertheless, a larger proportion of urea may be used, i.e. an F/U ratio of less than 1:1, which leads to an even greater reduction of the amount of formaldehyde in the distillates, but as a result, a solution is obtained at the foot that will require an additional treatment for its application to the preparation of glues or resins.

The temperature of the scrubbing liquid solution should be in the range of 92–100° C., preferably in the range of 94° to 98° C. At this operating temperature the formaldehyde vapor pressure of the scrubbing liquid solution is relatively high, whereby it is necessary for the fresh urea solution to be supplied at the upper region of the scrubbing column in order to retain all the formaldehyde separated out of said liquid scrubbing solution.

In a variant of the invention and with the purpose of maintaining the temperature of the scrubbing liquid solution below the above-mentioned values so as thereby to reduce the proportion of formaldehyde given off, a pressure below atmospheric pressure is used. In this way the temperature can be controlled and the separation of the trioxane from the formaldehyde can be promoted.

In another variant of the invention, if it is wanted to limit the production of urea-formaldehyde precondensates, the trioxane-formaldehyde-water mixture (or trioxane and formaldehyde aqueous mixture) to be scrubbed in a separate scrubbing column with the urea solution, is the one that is distilled at the head of the distillation column used in a conventional production process like the one described at the beginning of the text. In this case, the distillate from said distillation column contains a lower formaldehyde concentration and on the other hand this concentrates at the foot of the distillation column. If the concentration of the solution at the foot of said distillation column is sufficiently high, it may be reccirculated to the reactor, if it were not, it must be concentrated in an adjoining facility. In this variant, the formaldehyde solution returned to the reactor is accompanied by a certain amount of trioxane that, as already said at the beginning, reduces the conversion rate in the reactor.

Both in one case and in the other, the trioxane-water azeotrope is obtained at the head of the urea scrubbing column in the form of vapour that condenses and the trioxane is subsequently crystallized from said condensate by cooling. The small amounts of impurities that accompany it are easily removed together with the mother liquors. The separation and later purification process can follow any of the ways already described in the literature and does not form a part of the present invention.

Vapors coming from a trioxane synthesis reactor, or vapors exiting a head of a distillation column of a conventional process, are supplied to the scrubbing column 1 at point 2. They form an aqueous trioxane and formaldehyde mixture. Said vapors (or aqueous trioxane and formaldehyde mixture) are scrubbed in the scrubbing column 1 with the recirculating scrubbing liquid. This scrubbing liquid is extracted from the foot 3 of the scrubbing column 1 and is reinserted in part in the scrubbing column 1 by a pump 4 at point 6. A urea and sodium hydroxide solution is supplied into the scrubbing column 1 at an upper region 7 thereof and a trioxane-water azeotrope is obtained through the head 8 of said scrubbing column 1. From the lower exit 5 there is removed from the current of scrubbing liquid extracted at the foot 3 of the scrubbing column 1 an amount of formaldehyde corresponding to the formaldehyde supplied at point 2 and it is taken to a facility for the production of urea-formaldehyde resins.

Figure 2:
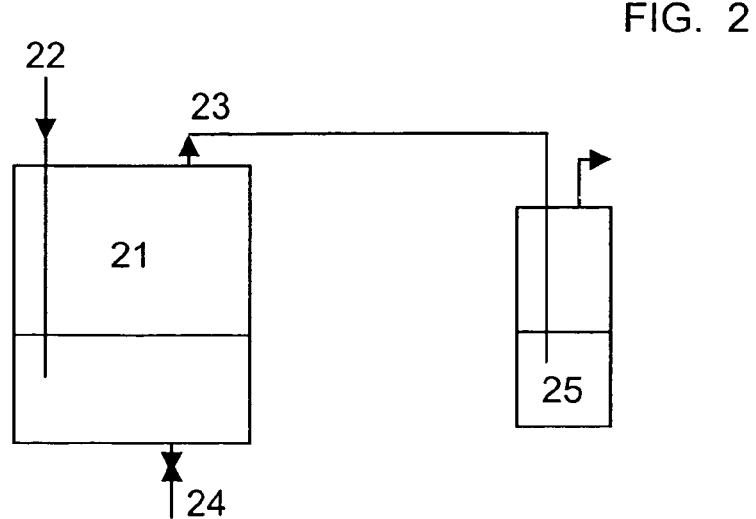
FIG. 2 is a schematic view of facility used for the realization of the example.

In the following examples the effectiveness of the treatment with urea is demonstrated. The facility used to carry out these experiments is as shown in FIG. 2. The mixture of trioxane, formaldehyde, water and urea is introduced in the reactor having a double thermostatted jacket 21 provided with a reactant inlet tube 22 and a vapor outlet tube 23 as well as with a sampling point 24. The pH of the mixture is adjusted with a sodium hydroxide solution and the mass is heated to boiling point. The vapors produced are absorbed in water contained in appropriate water scrubbers 25. The content of the reactor 21 and the liquors of the water scrubbers 25 are sampled at set intervals of time and the formaldehyde and trioxane content thereof are determined.

In the following examples, reflected in Table 1, the influence of the amount of added urea as well as the effect of the pH on the formaldehyde emission in the vapors is seen. As a measure of the effectiveness of the process the % Trioxane/% Formaldehyde (T/F) ratio and the "enrichment" R, defined as the ratio of the T/F ratios in the distillate and in the reactor, respectively, is given.

Example number 1, without urea, is taken as a reference.

TABLE 1

| Operation | 1 | 2 | 3 | 4 | 5 | 6 | 7 |
|---|---|---|---|---|---|---|---|
| Reactor | | | | | | | |
| Formaldehyde % | 20.6 | 19.1 | 16.2 | 16.9 | 18.4 | 19.8 | 26.7 |
| Trioxane % | 30.0 | 27.3 | 23.1 | 23.1 | 26.3 | 28.1 | 2.6 |
| Water % | 49.4 | 44.5 | 37.7 | 37.1 | 43 | 45.9 | 62.3 |
| Urea % | 0 | 9.1 | 23 | 23 | 12.3 | 6.2 | 8.4 |
| pH | 5.4 | 5.5 | 5.5 | 7.5 | 5.4 | 7.2 | 7.5 |
| F/U mol/mol | | 4.2 | 1.4 | 1.47 | 3.0 | 6.4 | 6.35 |
| % TOX/% F | 1.46 | 1.43 | 1.43 | 1.37 | 1.43 | 1.42 | 0.098 |
| Distillate | | | | | | | |
| Formaldehyde % | 11.6 | 6.4 | 2.5 | 1.2 | 5.4 | 6.4 | 17.8 |
| Trioxane % | 64.7 | 60.5 | 62.6 | 67.3 | 58.8 | 60.2 | 7.9 |
| Water % | 23.7 | 33.1 | 34.9 | 31.5 | 35.8 | 33.4 | 74.3 |
| % TOX/% Form. | 5.6 | 9.4 | 24.7 | 56.1 | 6.4 | 9.4 | 0.44 |
| Enrichment R | 3.8 | 6.6 | 17.3 | 40.9 | 4.5 | 6.6 | 4.5 |

The invention claimed is:

1. A process for the separation of an aqueous mixture of trioxane and formaldehyde, said mixture having a first trioxane to formaldehyde ratio, said process comprising the steps of
   reacting the aqueous mixture of trioxane and formaldehyde, which is in vapor phase, with a urea solution;
   wherein said reacting step includes the steps of scrubbing said aqueous mixture of trioxane and formaldehyde with the urea solution in a scrubbing column; and
   separating an exiting vapor phase and an exiting liquid phase,
   wherein said exiting vapor phase has a second trioxane to formaldehyde ratio that is higher than said first trioxane to formaldehyde ratio and said exiting liquid phase is a urea-formaldehyde solution, and
   wherein, at a foot of said scrubbing column, a formaldehyde to urea molar ratio is between 1:1 and 6:1.

2. The process of claim 1, further comprising the step of adding a dilute solution of a strong base at a head of said column together with said urea solution.

3. The process of claim 1, wherein said formaldehyde to urea molar ratio is between 4:5:1 and 5:5:1.

4. The process of claim 1, wherein said urea solution at said foot of said column has a temperature ranging from 92° to 100° C.

5. The process of claim 4, wherein said urea solution at said foot of said column has a temperature ranging from 94° to 98° C.

6. The process of claim 1, wherein said scrubbing column operates at an internal pressure equal to or lower than atmospheric pressure.

7. The process of claim 1, wherein said urea solution at said foot has a pH above 5.

8. The process of claim 7, wherein said urea solution at said foot has a pH ranging from 7 to 9.

9. The process according to claim 1, further comprising the step of obtaining the trioxane from a reactor in which trioxane is being synthesized.

10. The process of claim 9, further comprising the step of synthesizing the trioxane in said reactor starting from an aqueous solution of formaldehyde in the presence of an acid catalyst.

11. The process according to claim 1, further comprising the step of deriving said aqueous mixture of trioxane and formaldehyde from a distillation column in which a prior aqueous mixture of trioxane and formaldehyde is separated from excess formaldehyde.

12. The process according to claim 11, further comprising the step of distilling said prior aqueous mixture of trioxane and formaldehyde coming from a reactor in which trioxane is being synthesized from an aqueous solution of formaldehyde.

13. The process according to any one of claims 1, 2, 3, 4, 5, 6, 7 and 8, further comprising the step of using the urea-formaldehyde solution in the production of urea-formaldehyde glues or resins.

* * * * *